US 6,559,938 B1

(12) United States Patent
Smedt

(10) Patent No.: US 6,559,938 B1
(45) Date of Patent: *May 6, 2003

(54) BACKSIDE CONTAMINATION INSPECTION DEVICE

(75) Inventor: Rodney G Smedt, Los Gatos, CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/714,042

(22) Filed: Nov. 16, 2000

Related U.S. Application Data

(63) Continuation of application No. 09/299,698, filed on Apr. 26, 1999, now Pat. No. 6,204,917.
(60) Provisional application No. 60/101,400, filed on Sep. 22, 1998.

(51) Int. Cl.[7] .................................................. G01N 21/00
(52) U.S. Cl. ...................... 356/237.5; 356/337; 356/338
(58) Field of Search ............................... 356/237.5, 337, 356/338

(56) References Cited

U.S. PATENT DOCUMENTS

| 3,982,627 | A | | 9/1976 | Isohata | |
| 4,376,482 | A | | 3/1983 | Wheeler et al. | |
| 4,407,627 | A | | 10/1983 | Sato et al. | |
| 4,441,853 | A | | 4/1984 | Kosugi | |
| 4,887,904 | A | * | 12/1989 | Nakazaeto et al. | 356/375 |
| 4,892,455 | A | | 1/1990 | Hine | |
| 5,052,886 | A | | 10/1991 | Moroi | |
| 5,208,648 | A | * | 5/1993 | Batchelder et al. | 356/237 |
| 5,298,989 | A | * | 3/1994 | Tsukahara et al. | 348/126 |
| 5,352,249 | A | | 10/1994 | Vollaro | |
| 5,425,846 | A | | 6/1995 | Koze et al. | |
| 5,661,408 | A | * | 8/1997 | Kamieniecki et al. | 324/765 |
| 5,700,297 | A | | 12/1997 | Vollaro | |
| 6,177,989 | B1 | * | 1/2001 | Bruce | 356/237.5 |
| 6,204,917 | B1 | * | 3/2001 | Smedt | 356/237.5 |

* cited by examiner

Primary Examiner—Frank G. Font
Assistant Examiner—Philip Natividad
(74) Attorney, Agent, or Firm—Smyrski & Livesay, LLP

(57) ABSTRACT

A system for simultaneously inspecting the frontsides and backsides of semiconductor wafers for defects is disclosed. The system rotates the semiconductor wafer while the frontside and backside surfaces are generally simultaneously optically scanned for defects. Rotation is induced by providing contact between the beveled edges of the semiconductor wafer and roller bearings rotationally driven by a motor. The wafer is supported in a tilted or semi-upright orientation such that support is provided by gravity. This tilted supporting orientation permits both the frontside and the backside of the wafer to be viewed simultaneously by a frontside inspection device and a backside inspection device.

23 Claims, 3 Drawing Sheets

BACKSIDE CONTAMINATION INSPECTION DEVICE

This is a continuation of U.S. patent application Ser. No. 09/299,698 Apr. 26, 1999, now U.S. Pat. No. 6,204,917, which claims the benefit of U.S. Provisional Application No. 60/101,400, filed Sep. 22, 1998.

BACKGROUND OF THE INVENTION

1. Field of the Invention

The present invention relates generally to contamination inspection for semiconductor wafers and the like and in particular to a system which inspects both the frontside and backside of a semiconductor wafer without manual or automatic inversion of the wafer.

2. Description of the Related Art

Tools used in the semiconductor wafer manufacturing process must periodically be checked to determine whether they must be replaced or are still in usable condition. The condition of a tool is checked by inspecting wafers processed by that tool for defects. Bare wafers are typically routed through the process tool with the frontside facing up, and wafer defects detected optically by illuminating portions of the wafer and measuring the amount of illuminating light scattered by defects on the wafer surface.

Previously, systems which performed inspection of wafers did so in two discrete stages. First, the frontside of the wafer was scanned for contamination caused by the process tool. If the defect rate on the frontside of the wafer was acceptable, the wafer was then turned over to inspect the backside for further particle contamination and other defects. The process tool was considered usable if the defect rate on the backside of the wafer was also acceptable.

Inspection of both sides of a wafer by these procedures accordingly required time for inspection of one side, examination of the one side, inverting the wafer without excessively damaging the wafer, scanning the reverse side, and examining the results of the second side scan. In addition to this excessive amount of time required for examination, the process of flipping the semiconductor wafer had a tendency to contaminate the edges of the wafer due to surface or edge contact with a gripping device. In some processes, when the wafer was flipped over to inspect the backside, the front side of the wafer could be contaminated by the flipping process. The resulting contamination of the frontside of the wafer tends to render the wafer unsuitable for further processing. Thus, all test wafers were usually scrapped after each inspection, reducing overall productivity and increasing per unit cost.

Edge handling of wafers has also complicated the problem. As wafers tend to suffer from contamination or other degradation when handled by wafer orientation systems, the handling of a wafer requires special care. Although previous wafer orientation systems have included multiple drive rollers, radially inwardly-biased contact rollers, and a tiltable wafer-supporting table with an air-bearing mechanism, each of these handling methods have benefits and drawbacks. Systems without multiple drive rollers and radially inwardly-biased or spring-loaded contact rollers cannot maintain steady wafer rotation rate during the portion of a cycle in which the drive roller is not in contact with the round edge of the wafer because the drive roller loses traction along the wafer edge.

In inspection equipment, it is important to maintain steady rates of wafer rotation to avoid errors in defect detection, such as errors in detecting defects where none exist, or simply failing to detect defects. Previous systems which supported semiconductor wafers through direct contact with a solid surface present special problems during inspection since contact with the support surface may increase contamination or move defects from one location to another in ways that render the wafer unsuitable for future processing.

It is therefore an object of the current invention to provide a system for minimizing the time required for full inspection of both the front side and back side of a wafer.

It is another object of the current invention to provide an arrangement which minimizes overall wafer contamination during the inspection process, particularly when inspecting both front and back sides of the wafer.

It is a further object of the current invention to minimize edge handling concerns, such as contamination, during the inspection of the front side and back side of a wafer.

It is still a further object of the current invention to minimize the number of defects missed or falsely detected by the inspection system.

SUMMARY OF THE INVENTION

According to the present invention, there is provided an apparatus that simultaneously inspects the frontsides and backsides of semiconductor wafers for defects. The inventive system disclosed herein may also read tracking information imprinted on the backsides of the semiconductor wafers.

The invention rotates the semiconductor wafer while the frontside and backside surfaces are generally simultaneously optically scanned for defects. Rotation is induced by providing contact between the beveled edges of the semiconductor wafer and roller bearings rotationally driven by a motor.

In the present invention, a semiconductor wafer is supported such that the semiconductor wafer lays flat during the inspection process. The surface is large enough to accommodate the wafer as well as the rollers for rotating the wafer and the means for holding the wafer. The wafer is preferably supported in a tilted or semi-upright orientation such that support is provided by gravity. This tilted supporting orientation permits both the frontside and the backside of the wafer to be viewed simultaneously by a frontside inspection device and a backside inspection device. The backside of the wafer for purposes of this invention is the side of the semiconductor wafer by which the wafer is being supported. Simultaneous dual-side inspection of the front side and back side of the wafer effectively doubles the throughput of inspection equipment and eliminates the need to turn the semiconductor wafer over during the inspection process, thereby reducing the opportunity for edge contamination of the inspected wafer.

The wafer is rotated by multiple motor-driven roller bearings. These drive rollers are positioned at the circumference of the wafer and are angled such that the roller pads contact the wafer only along the beveled edge. This periphery positioning and rotation coupled with angular contact between the rollers and wafer edge and surface permits inspection of the entire surface and significantly reduces the potential for contamination of the surface resulting from edge contact, or contact with the roller pads.

The drive rollers are spaced apart such that at least one of the two drive rollers spaced farthest apart contacts the round edge of the wafer throughout the rotation cycle. This constant contact feature ensures that the rotation rate of the wafer is suitably steady during defect inspection. Also, the steady rotation rate minimizes the number of defects missed or falsely detected by the inspection system.

The wafer rotation rate is such that roller contact does not damage the wafer edge. Furthermore, defects are not carried or transported from one part of the edge to another. Moreover, the rate should be controlled so as to minimize slip between the roller and the wafer edge. The present invention is intended for use at wafer rotation rates on the order of 400 revolutions per minute. Unlike previous systems, the present invention does not exhibit excessive vibration for defect inspection purposes at these rotation rates. The increased wafer rotation rate also increases the throughput of inspection equipment.

The semiconductor wafer is held against the drive rollers by pressure using a set of undriven roller bearings (contact rollers) or alternatively simply using gravitational force by tilting the wafer and inspection surface. This pressure ensures that the drive rollers hold traction on the beveled wafer edge so that a steady rotation rate can be maintained. All contact rollers thereby maintain contact with the edge of the semiconductor wafer throughout the rotation cycle.

Prior to inspection, the system locates the edge registration feature, commonly called the "flat". The system detects the specific position of the wafer using the edge registration feature either by measuring the position of the contact rollers, or by connecting the contact rollers to switches which are turned on when the contact rollers are touching a flat registration edge calibration switch. Once the flat registration edge or notch is located, the system rotates the wafer to desired orientations for inspection purpose by controlling the drive rotors.

Other objects, features, and advantages of the present invention will become more apparent from a consideration of the following detailed description and from the accompanying drawings.

DETAILED DESCRIPTION OF THE INVENTION

Figure 1:
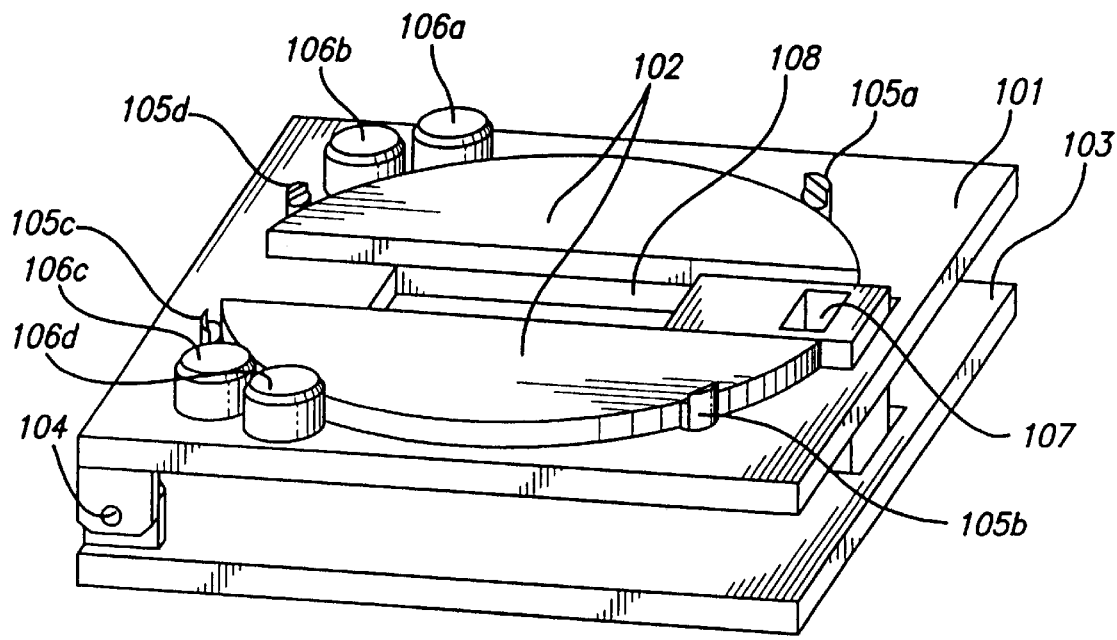
FIG. 1 illustrates a perspective view of the preferred embodiment of the invention in an unloaded state.
Figure 2:
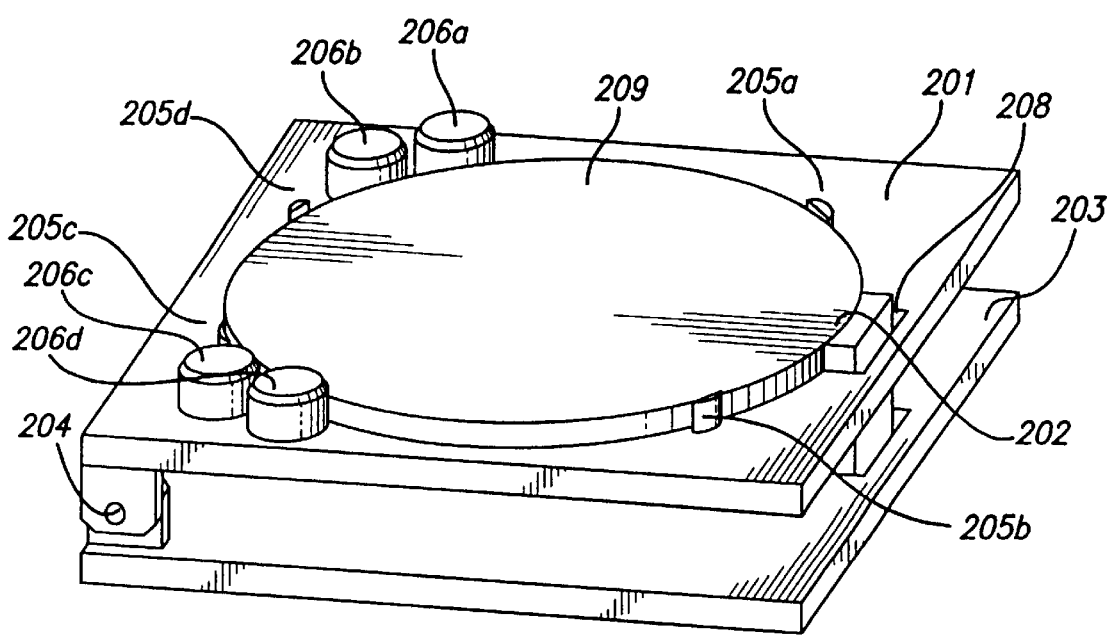
FIG. 2 presents a perspective view of the preferred embodiment of the invention loaded with a semiconductor wafer to be inspected.
Figure 3:
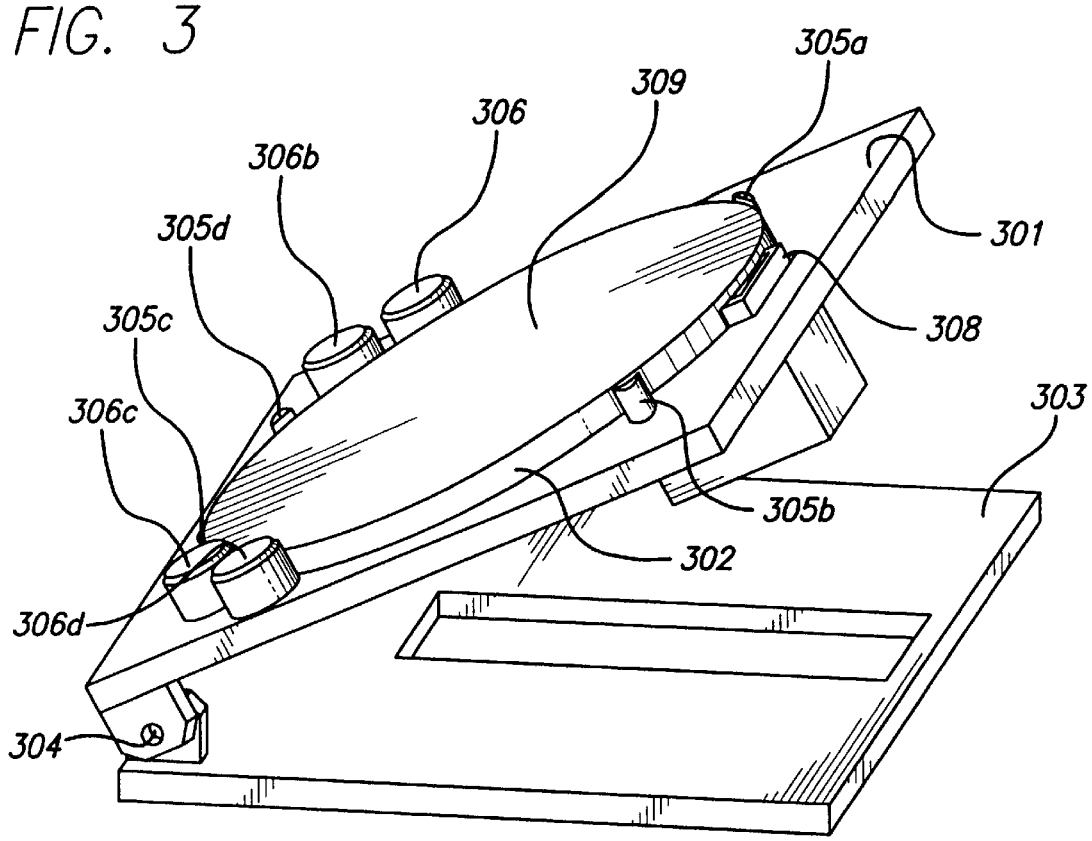
FIG. 3 is a perspective view of the preferred embodiment of the invention with the semiconductor wafer loaded and the table surface tilted in the scan position.

FIGS. 1–3 present various views of the invention in the loaded and unloaded states. From FIG. 1, the background contamination inspection device is initially in its unloaded state, or without a semiconductor wafer located thereon. The semiconductor wafer is supported by a substantially flat table surface 101. The substantially flat table surface 101 is equipped with an air-bearing mechanism 102 upon which the semiconductor wafer may be floatably supported to eliminate contamination of the backside by contact with the table surface 101. The table surface 101 is mounted to a fixed base 103 such that the table surface 101 can tilt about an axis 104 defined at a side edge of the table surface 101. Four wafer load pins 105a–105d are mounted on the table surface 101 such that they can retract and temporarily maintain the wafer. The wafer load pins 105a–d are located in a circular pattern concentric with the air-bearing mechanism 102 and semiconductor wafer which is to be loaded. Furthermore, the wafer load pins 105a–d are located proximate the round edge of the semiconductor wafer to be loaded.

Roller bearings 106a–d are rotatably mounted on the table surface 101 in an orientation substantially equivalent to the angle or axis 104 about which the table surface 101 is tilted. Roller bearings 106a–d are further arranged in a circular pattern having substantially the same center as the air-bearing mechanism 102 and the semiconductor wafer to be loaded such that the radius of the smallest circle simultaneously tangent to all of the roller bearings 106a–d is equal in length to the radius of the semiconductor wafer to be loaded. As shown in FIG. 1, roller bearings 106a and 106b are driven by motors (not shown) and are separated by such a distance that both cannot simultaneously contact the flat, or registration edge, in the semiconductor wafer. Thus roller bearings 106a–d provide continuous driving of the wafer when loaded thereon.

Prior to inspection, the system locates the edge registration feature, commonly called the "flat". The system detects the specific position of the wafer using the edge registration feature either by measuring the position of the contact rollers, or by connecting the contact rollers to switches which are turned on when the contact rollers are touching a flat registration edge calibration switch. Once the flat registration edge or notch is located, the system rotates the wafer to desired orientations for inspection purpose by controlling the drive rotors.

The scan head 107 is situated within the table channel 108. Table channel 108 passes completely through the top and bottom surfaces of table surface 101. The table channel 108 is symmetric about the radius of the semiconductor wafer and is of such length that the scan head 107 may travel from a position directly beneath the center of the semiconductor to a position directly under the outer edge of the wafer. The preferred scan head is shown in greater detail in FIG. 4.

FIG. 2 shows the preferred embodiment of the invention having the semiconductor wafer 201 loaded thereon. The semiconductor wafer 201 is floatably supported by the air-bearing mechanism 202. During the loading process, the wafer load pins 206a–d hold and center the semiconductor wafer 201 over the air-bearing mechanism 202. Once the operator or software determines that the semiconductor wafer 201 is centered over the table surface 201, the wafer load pins 206a–d are partially retracted and no longer contact the edge of the semiconductor wafer 201.

FIG. 3 shows the background contamination inspection device in scan position. The table surface 101 in FIG. 3 has been tilted to a predetermined angle about axis 304. The driven roller bearings 306a and 306b are continuously kept in contact with the wafer edge by the gravitational force acting on the semiconductor wafer 301 due to tilting. The tilting of the semiconductor wafer 301 permits high speed rotation of the semiconductor wafer and minimizes the amount of pressure exerted on the edge of the wafer 301 while still ensuring that at least one drive roller maintains contact and traction along the edge of the wafer throughout the wafer rotation cycle. Edge contact is therefore minimized since no undriven contact rollers are needed.

The wafer loading pins 305a–d are fully retracted when the invention is in the scan position and thus only contact the semiconductor wafer during the loading phase of the inspection. The wafer loading pins 305a–d do not contact the wafer during rotation or while the system is in the inspection phase.

Once the semiconductor wafer 301 has been loaded onto the table surface 301, the wafer loading pins 305a–d are retracted, the table surface 301 tilted as shown in FIG. 3, and the drive rollers 306a and 306b are turned to rotate the semiconductor wafer 301. The semiconductor wafer 301 is rotated by the motor (not shown) turning the drive rollers 306a and 306b. Positioned within the table surface 301 is the scan head 307 (not shown) which traverses in a linear manner to scan the backside of the semiconductor wafer 301, i.e. the side of the wafer adjacent to the table surface 301. The scan head 307 is positioned within the table surface channel 308 such that the orientation of the scan head 307 does not change relative to the semiconductor wafer 301 as the table surface 301 is tilted to the position shown in FIG. 3. During rotation of the table surface 301, the scan head 307 translates linearly within table surface channel 308 in a parallel orientation with respect to the bottom surface of the semiconductor wafer 301. While the semiconductor wafer 301 rotates adjacent to the wafer table 301 using drive rollers 306a and 306b, the scan head 307 translates within the table surface channel 308, moving from the edge of the semiconductor wafer 301 to the center thereof, or vice versa.

Various tilting angles may be employed in the current system while still within the scope of the present invention. The current desired tilting angle for the table surface is 45 degrees, but higher angles may be used successfully depending on the speed of the rotation of the semiconductor wafer 301 and the size and particularly weight of the wafer 301. For example, an excessively high angle between the table surface 301 and the horizontal may cause the wafer 301 to fall away from the table surface, while a relatively small angle between the table surface 301 and the horizontal may cause the wafer 301 to lose contact with the drive rollers 306a and 306b. It is therefore preferable to maintain the angle of tilt within the range of 15 degrees from horizontal to 75 degrees from horizontal.

Figure 4:
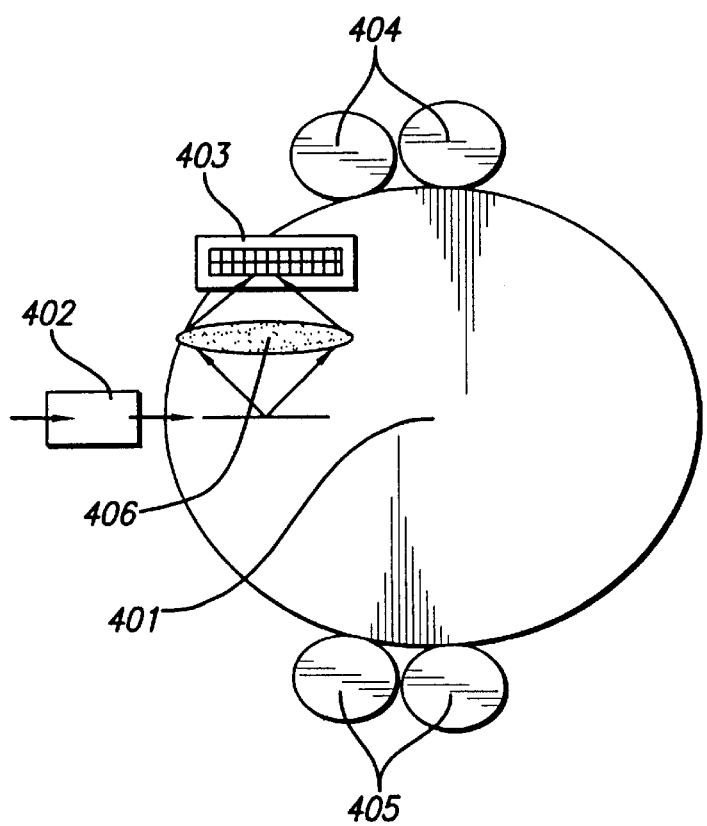
FIG. 4 is a plan view of an arrangement including the loaded semiconductor wafer, roller bearings and scan head elements.

FIG. 4 illustrates the backside inspection process. Backside inspection is preferably performed using the double-dark field method. Roller bearings 404 are rotated by a drive motor (not shown) to induce rotation of the semiconductor wafer 401. The roller bearings 404 illustrated in FIG. 4 represent an alternate orientation of the roller bearings from those shown in FIGS. 1–3. The roller bearings 404 of FIG. 4 and the undriven roller bearings 405 may be originally oriented away from the table surface (not shown) for purposes of loading the wafer 401 onto the table surface, and then the driven and undriven roller bearings may be repositioned adjacent the wafer 401 to provide sufficient but not excessive contact between the bearings 404 and 405 and the wafer 401.

The orientation of the elements illustrated in FIG. 4 contemplates a horizontal and untilted arrangement of the wafer and bearings, but the optical elements of FIG. 4 may be used in the tilted orientation of the invention illustrated in FIGS. 1–3.

In FIG. 4, the wafer 401 maintains contact with both the driven roller bearings 404 and the undriven roller bearings 405. During operation, as semiconductor wafer 401 rotates, the scan head 407 (not shown), including laser illuminator 402 and sensor 403, travels along the table surface channel (not shown) in close proximity to the surface being scanned. The sensor 403 may include one or more CCD detector elements. The laser illuminator 402 projects an elongated illuminating beam onto an area roughly 50 $\mu$m×10 mm in size, illustrated by the illuminated patch 406 in FIG. 4, on the surface of the semiconductor wafer 401 at a non-normal angle of incidence.

Figure 5:
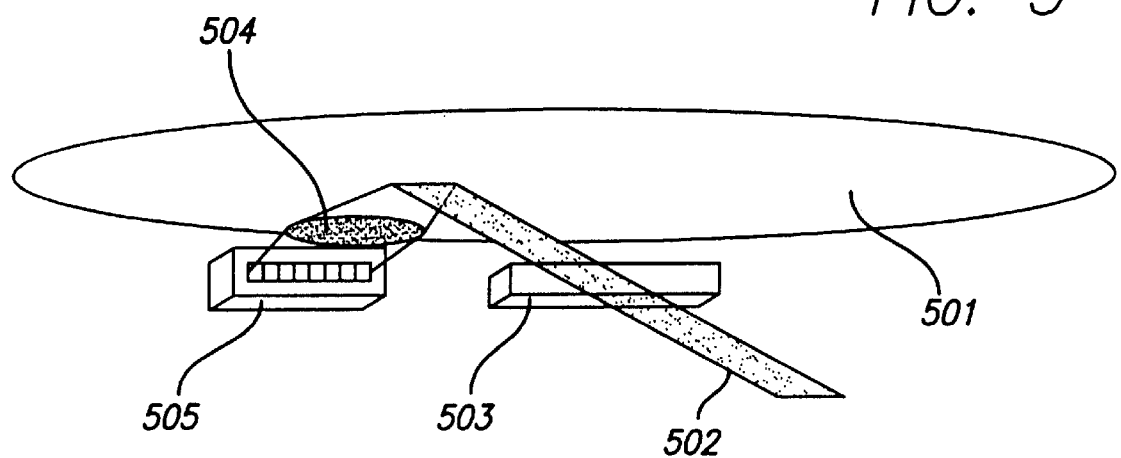
FIG. 5 presents a perspective view of the scan head CCD detector elements arranged in relation to the surface of the semiconductor wafer during backside inspection.

FIG. 5 shows the arrangement of the CCD detector elements relative to the semiconductor wafer 501. The illuminator (not shown) projects collimated beam 502 through cylindrical lens 503 onto illuminated patch 504 on the surface of the semiconductor wafer 501. CCD detector elements 505 are symmetrically located on either side of and parallel to the incident plane (the plane formed by the intersection of the wafer surface normal and the illumination path). The CCD detector elements 505 are linear and produce a serial read-out which corresponds to the amount of scattered light received by the detector. This output is used to determine whether a defect exists at the particular section of the wafer being examined. Using this information, the system determines whether the wafer 501 may be used in further processing. If the system determines that the wafer 501 is not usable, the process tool must be replaced and the wafer 501 is scrapped. If the wafer 501 is usable, the defect location information for the particular wafer is stored with its tracking number. The wafer 501 is then placed back in the processing stream and the process tool is not replaced.

Figure 6:
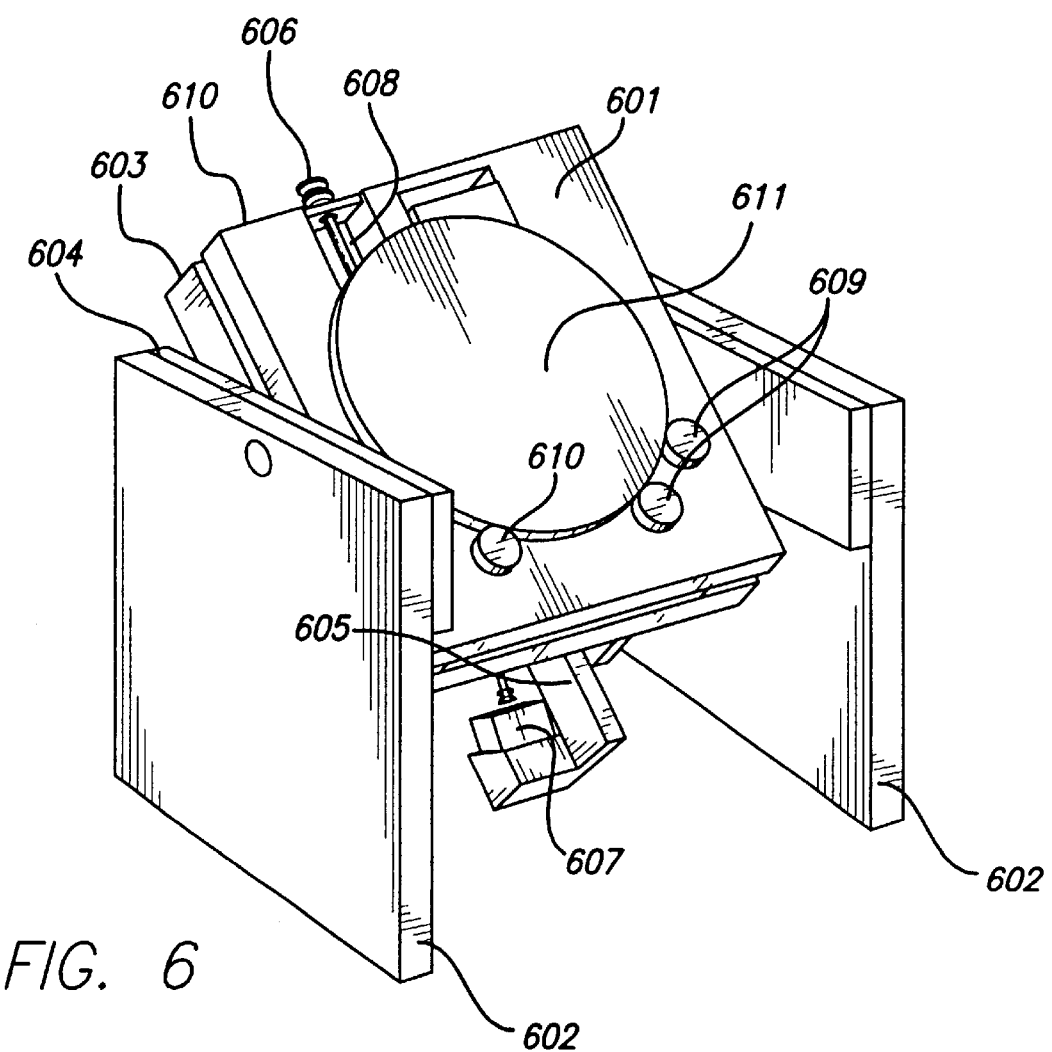
FIG. 6 illustrates a perspective view of an alternate embodiment of the present invention.

FIG. 6 illustrates an alternate, stand-alone embodiment of the present invention. In this embodiment, the table surface 601 is affixed to base 603. Base 603 is mounted to support legs 602 such that the base 603 may be rotated about axis 604. Scan head 607 is fixedly mounted to arm 605, and arm 605 is attached to turning screw 606. Turning screw 606 is rotationally coupled to a motor (not shown).

Rotation of turning screw 606 causes arm 605 and scan head 607 to move laterally along the table surface channel 608, parallel to the backside of semiconductor wafer 611 in its tilted state (as shown) or untilted state. This motion of the scan head 607 permits scanning of the back side of the semiconductor wafer 611. The semiconductor wafer 611 is rotated by contact with roller bearings 609 which are driven by a motor (not shown). The semiconductor wafer 611 also maintains contact with roller bearing 610 (second roller bearing not shown), which is undriven. The contact with undriven roller bearing 610 is due to gravitational force being exerted on the semiconductor wafer 611. Thus the orientation of the wafer, as shown, is in constant contact with the rollers and may be inspected on both front and back sides.

While the invention has been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

I claim:

1. A device for inspecting a semiconductor wafer, said semiconductor wafer comprising a front side and a back side, comprising:

a first illuminator positioned proximate the back side of said semiconductor wafer for directing energy to said back side of said semiconductor wafer;

a second laser illuminator positioned proximate the front side of said semiconductor wafer for directing energy to said front side of said semiconductor wafer; and means for rotating said semiconductor wafer, wherein said first illuminator moves substantially parallel to the semiconductor wafer while said rotating means rotate said semiconductor wafer.

2. The device of claim 1, further comprising a plurality of roller elements for rotating said semiconductor device.

3. The device of claim 1, further comprising a support surface for mounting said semiconductor wafer.

4. The device of claim 3, wherein said support surface is partially open to permit inspection of said wafer therethrough.

5. The device of claim 3, further comprising an air bearing integrated into said surface for floatably supporting said semiconductor wafer.

6. The device of claim 2, further comprising a drive motor for rotating at least one of said plurality of roller elements.

7. The device of claim 3, further comprising means for tilting said support surface to a predetermined angle.

8. A method for inspecting a specimen, said specimen having a front side and a back side, comprising:

inspecting the back side of said specimen by moving an inspection apparatus substantially parallel to the back side of the specimen; and simultaneously inspecting the front side of said specimen.

9. The method of claim 8, wherein said specimen comprises a semiconductor wafer.

10. The method of claim 8, further comprising floatably supporting said specimen on a surface.

11. The method of claim 10, further comprising rotating said specimen.

12. The method of claim 8, wherein said inspecting comprises illuminating and viewing the back side of said specimen.

13. The method of claim 12, wherein said simultaneously inspecting comprises illuminating and viewing the back side of said specimen.

14. The method of claim 10, further comprising tilting said surface and said specimen to a predetermined angle.

15. The method of claim 11, wherein rotating comprises driving at least one roller in contact with said specimen.

16. A method for simultaneously inspecting both a front side and a back side of a semiconductor wafer, comprising:

rotating said wafer;

imparting light energy to the front side of said rotating wafer and simultaneously imparting light energy to the back side of said rotating wafer using an inspection apparatus moving substantially parallel to the back side of the rotating wafer; and receiving light energy reflected from said front side and said back side of said rotating wafer.

17. The method of claimed 16, further comprising floatably supporting said semiconductor wafer on a surface.

18. The method of claim 17, further comprising rotating said semiconductor wafer.

19. The method of claim 16, wherein said imparting comprises illuminating the back side of said semiconductor wafer with light energy and illuminating the front side of said semiconductor wafer with light energy.

20. The method of claim 19, wherein said receiving comprises acquiring light energy reflected from the front side of said semiconductor wafer and acquiring light energy reflected from the back side of said semiconductor wafer.

21. The method of claim 17, further comprising tilting said surface and said semiconductor wafer to a predetermined angle.

22. The method of claim 18, wherein rotating comprises driving at least one roller in contact with said specimen.

23. A device for simultaneously inspecting a front side and a back side of a semiconductor wafer, comprising:

a first inspection device positioned proximate the back side of said semiconductor wafer for inspecting said back side of said semiconductor wafer by moving substantially parallel to said back side of said semiconductor wafer;

a second inspection device positioned proximate the front side of said semiconductor wafer for inspecting said front side of said semiconductor wafer; and means for rotating said semiconductor wafer, wherein said first inspection device moves substantially parallel to the semiconductor wafer while said rotating means rotate said semiconductor wafer;

wherein said first inspection device and said second inspection device have the ability to inspect substantially all of the front side and the back side of the semiconductor wafer with substantially no obscuration.

* * * * *